United States Patent [19]

Fankhauser et al.

[11] 4,391,275

[45] Jul. 5, 1983

[54] METHOD FOR THE SURGICAL TREATMENT OF THE EYE

[75] Inventors: Franz Fankhauser; Eugen van der Zypen, both of Bern; Philippe Roussel, Thun, all of Switzerland

[73] Assignee: Lasag AG, Thun, Switzerland

[21] Appl. No.: 211,202

[22] Filed: Nov. 28, 1980

[30] Foreign Application Priority Data

Nov. 28, 1979 [CH] Switzerland ............... 10570/79
Mar. 5, 1980 [FR] France ...................... 80 04994

[51] Int. Cl.³ ............................................ A61B 17/36
[52] U.S. Cl. .................................. 128/303.1; 128/362
[58] Field of Search ............... 128/303.1, 362, 395, 128/399

[56] References Cited

U.S. PATENT DOCUMENTS

| 4,164,222 | 8/1979 | Prokhorov et al. | 128/303.1 |
| 4,185,633 | 1/1980 | Prozorov et al. | 128/303.1 |
| 4,215,694 | 8/1980 | Isakov et al. | 128/303.1 |
| 4,266,549 | 5/1981 | Kimura | 128/303.1 |
| 4,270,845 | 6/1981 | Takizawa et al. | 128/303.1 |
| 4,273,535 | 6/1981 | Yamamoto et al. | 128/303.1 |
| 4,309,998 | 1/1982 | Aron et al. | 128/303.1 |

*Primary Examiner*—Kyle L. Howell
*Assistant Examiner*—Max F. Hindenburg
*Attorney, Agent, or Firm*—Berger & Palmer

[57] ABSTRACT

The invention relates to a method for the surgical treatment of the eye by perforation, by laser radiation, of a tissue or inner wall of the eyeball having a resistance to the free circulation of the aqueous humour. A laser radiation burst comprising at least one pulse of duration d comprised between 10 and 60 ns and of radiated energy comprised between 30 and 300 millijoules is produced and focussed at a determined distance p inside the wall. The radiation is focussed according to a solid angle $\Omega$ determining a density of radiated energy causing ionization of the propagation medium.

A shock wave is also produced due to this ionization close to the mean direction of propagation of the radiated, thereby allowing the tissue or inner wall to be perforated.

13 Claims, 8 Drawing Figures

METHOD FOR THE SURGICAL TREATMENT OF THE EYE

BACKGROUND OF THE INVENTION

The invention relates to a process for the surgical treatment of the eye by perforation, by laser radiation, of a tissue or inner wall of the eyeball having a resistance to the free circulation of the aqueous humour. Such a method may be utilized for the treatment of eyeball diseases such as glaucoma in which the perforation of an inner wall of the eyeball is able to give the patient a substantial and swift improvement in health.

Glaucoma is an eye disease which is characterized mainly by an increase in the intra-ocular pressure. As is known, the intraocular pressure for the eye of a human in good health is comprised between 15 and 16 mm of mercury. In the case of a disease of the glaucoma type, the intra-ocular pressure of the eye afflicted by such a disease is more often above 20 to 21 mm of mercury and in the course of daily variations can reach, more often than not, pressures that are higher than the above mentioned pressures and variable according to the type of glaucoma. This excess pressure and its variations have as a consequence, in the end, the destruction of the optic nerve. The clinical symptoms, which are not very pronounced in the early stages of such a disease, are characterized mainly by a generally slow and progressive narrowing of the field of vision and by an insular degradation of the latter, ending in a total loss of vision in the absence of treatment.

Recent studies of epidemiology of glaucoma have shown that in the majority of industrial countries such a disease was the main cause of blindness. In Western Europe and the United States an ailment of this type attacks an average percentage in the order of 2% of individuals aged 40 years or more. In 60% of the cases of such a disease the outcome, if not treated, is inevitably blindness.

Other recent studies have revealed that in patients affected by diabetes, the average percentage of the existence of a disease of the glaucoma type was 16%.

The main different forms of glaucoma can be listed in the following way, their common primary cause appearing to be a localised resistance to the free circulation of the aqueous humour on the level of a determined location of the usual circuit of the aqueous humour between the posterior chamber and the anterior chamber of the eye or in the angle of the anterior chamber of the eye, the aqueous humour then normally reaching at this stage the vein system. The first effect of this increased resistance is an increase in the intra-ocular pressure of the eye and finally the appearance of the symptoms of glaucoma.

The primary glaucomas are:

Chronic glaucoma simplex or glaucoma angulo aperto which is generally characterized by an open irido-corneal angle. The zone of localized resistance to the free circulation of the aqueous humour is in this case situated on a level with the inner wall of the canal of Schlemm, the so-called trabecular meshwork, which separates the canal of Schlemm from the anterior chamber of the eye nearby the irido-corneal angle. The intra-ocular pressure in this case is above 22 mm of mercury and can exceed 40 mm of mercury. This kind of glaucoma also includes glaucoma capsulare and pigment glaucoma;

glaucoma with closed angle or glaucoma acutum angulo obstructo which is generally characterized by a closed irido-corneal angle, the iris on a level with the irido-corneal angle exerting a pressure on the inner wall of the canal of Schlemm causing, by closure, a resistance to the flow of the aqueous humour. This kind of glaucoma includes intermittent glaucoma in which closure is not permanent, the increase or decrease of the aqueous humour pressure occuring according to the iris-root position relative to the irido-corneal angle;

mixed glaucoma which is a combination of the above two types;

infantile glaucoma (Hydrophtalmus, Buphthalmus) which are to be related with congenital "failure". Generally this congenital failure consists of an abnormal deposition of embrionary substance on the irido-corneal angle inner walls.

Other forms of glaucoma can also be analysed; these are often so-called secondary forms as they are linked to other illnesses.

Some of them are to be related to an inflammation of the supraciliary space and of the iris, such an inflammation leading generally to a sticking of the iris-root with the inner walls of the anterior chamber of the eye thereby giving use to a possible increase of the aqueous humour pressure.

Others are to be related to the inflammation and swelling of the inner walls of the anterior chamber of the eye which leads also to an increase of the resistance to the free circulation of the aqueous humour.

Others one, the so-called glaucoma by obstruction of the pupillary block, arise from the peripheral sticking of the iris on the crystalline lens or on the front part of the vitreous humour when the crystalline lens has been removed.

Closing of the pupil through a membrane due to an inflammation (occlusion pupillae) will also lead to a particular secondary form of glaucoma.

Different approaches of therapeutic treatment of glaucoma have been proposed until now.

One method of therapeutic treatment by medicaments consists in controlling the intra-ocular pressure of the eye by local, oral or parenteral administration of medicaments as for example the medicament known by the name "Diamox". These methods have a limited use because on the one hand their effect is often not certain and, on the other hand, this effect is often not lasting in the long term.

Another method of therapeutic treatment by direct surgical intervention can also be envisaged. However, such a technique presupposes a first class hospital substructure, a very high qualification on the person carrying out the operation, and in any case allows success to be achieved in only a percentage of cases varying between 40 and 92% according to the type of intervention.

SUMMARY OF THE INVENTION

The method for the surgical treatment of the anterior chamber of the eye allows in a non limiting way the principal types of glaucoma that have been described above to be treated by the intervention of laser microsurgery.

The method for surgical treatment of glaucoma according to the invention aims at bringing certain, and if possible lasting, relief to the patient afflicted by such a disease. This result, according to the method of treatment of the invention, is obtained by the re-establishment of the free circulation of the aqueous humour by perforating the tissues of the eyeball situated in the region of the irido-corneal angle of the anterior chamber of the eye, or the iris, and accordingly, by the come back to a substantially normal intra-ocular pressure.

According to the invention, this result may be obtained either by the perforation of the wall separating the anterior chamber of the eye from the canal of Schlemm, this perforation being carried out, for example, on the level of the "trabecular meshwork", or by opening the supra-ciliary space and the supra-choroidal space, or by perforation of the iris by means of a laser beam in determined conditions of emission and focussing. Any method, in which the perforation of another region of the eyeball, allowing the re-establishment of the free circulation of the aqueous humour, is carried out in conditions like radiation and focussing of a laser beam does not depart from the scope of the present invention.

In particular this method allows, by reason of the localisation of the operation on the single zone of the eyeball that is to be perforated, the minimisation and the virtual reduction to zero of the risks of secondary harmful effects which can exist in the case of a classic surgical operation.

BRIEF DESCRIPTION OF THE DRAWINGS

The method for the surgical treatment of the anterior chamber of the eye will be described in more details in case of glaucoma treatment in the following description and the drawings in which.

DETAILED DESCRIPTION OF THE DRAWINGS

Figure 1A:
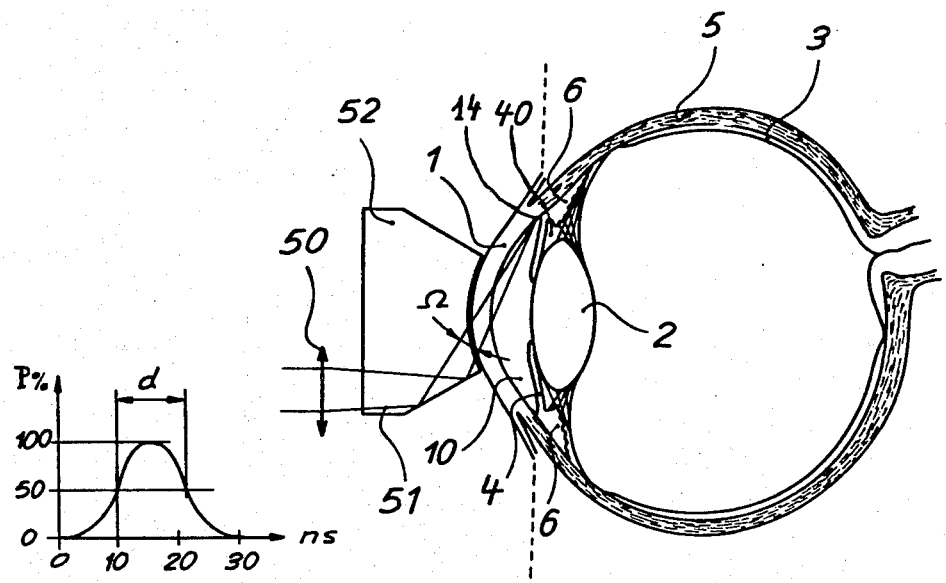
FIG. 1a represents, in a view from above in section of the eyeball of a left eye, the surgical treatment method of the eye according to the invention.

According to FIG. 1a, the method for the surgical treatment of the eye, as illustrated of the anterior chamber of the eye is carried out by treatment by laser beam irradiation. The eyeball shown in FIG. 1a comprises the cornea 1 allowing the transmission of the light beams through the crystalline lens 2 to the retina 3. The iris 4 is linked to the cornea 1 and to the sclera 5 by the intermediary of the ciliary body 6 which forms with the cornea 1 the irido-corneal angle 14 and with the iris the anterior chamber 10 and the posterior chamber 40 of the eye containing the aqueous humour. The method according to the invention consists in producing at least one laser radiation pulse as represented in FIG. 1a of duration d, measured at half peak power comprised between 10 and 60 ns. The radiated energy of the pulse is preferably comprised between 30 and 300 millijoules. Such laser radiation pulses can be produced by a system of laser emission of the Q type switched, for example. The laser radiation is focussed at a determined distance p inside the wall to be perforated according to a solid angle $\Omega$ determining a radiated energy density causing ionisation of the propagation medium.

In FIG. 1a, the focussing of the laser radiation is obtained by a converging system of lenses 50. Preferably the solid angle $\Omega$ has a semi-opening of the order of 10 degrees. According to the particular, non-limitative mode of treatment according to the method of the invention shown in FIG. 1a, the laser radiation beam 51 is transmitted towards the zone to be treated, the zone of the irido-corneal angle 14, by means of a contact glass 52 of the Goldmann type comprising reflection surfaces which allow the aiming of the reflected beam at the chosen zone to be treated. Preferably, the contact glass is constituted of a material tolerating the high density of power of the laser beam, glass of the BK7 type free from internal cooling restraints. Generally, the observation of the zone to be treated according to the doctor's diagnosis is before the treatment as such by laser beam emitted, and the emission of this radiation itself can advantageously be carried out with a guarantee of precision and effectiveness by means of the treatment device for glaucoma described in the following description.

The ionisation of the propagation medium allows, in the zone of the wall to be perforated, a shock wave substantially spherical and of maximum energy in the region of the mean direction of propagation of radiation to be produced. The shock wave of the spherical type substantially originates in the vicinity of the ionisation zone of the propagation medium in the region of the mean direction of propagation of the laser radiation, the so-called centre of ionisation. The initial pressure of this wave, which theoretically can reach $10^5$ atmospheres, decreases approximately in the ratio 100 at a distance of 1 mm from the centre of ionisation and then decreases as a function of the distance beyond. The energy transported by the shock wave is theoretically comprised between 10 and 50% of the energy of the laser pulse emitted, the complementary fraction being degraded in dissipated heat in an elementary volume of the propagation medium in which turbulence and cavitation phenomena are expected to occur. The corresponding temperature of the propagation medium during this degradation probably does not exceed a few tens of degrees beyond a spherical volume with a curvature radius of 300 $\mu$m. The phenomenon of piercing of the wall to be treated will probably be then attributed only to the mechanical effect of the shock wave, taking into account the choice of the focussing point of the laser radiation with respect to the wall to be perforated.

The operatives steps for carrying out the method according to our invention are to be defined as following after the careful examination of the anterior chamber of the eye to be treated by the doctor for final diagnosis on the actual disease.

At first sight, the focussing solid angle of the power laser radiation is fixed by the doctor at its maximal value in relation with the local configuration surrounding the tissue to be treated by perforation. Then, the focus of the power laser radiation will be settled with high accuracy on the tissue to be perforated. As it will be disclosed in the following description, the doctor may use for such a purpose an ancillary visible radiation of low energy which substantially will follow the same optical path as that of power laser radiation. A checking of the absence of any impingement of the optical path of the power laser radiation on the local configuration surrounding the tissue to be perforated will allow it to be kept clear from any unwanted effect on that local configuration. According to his preceeding diagnosis, the doctor will have then to shift the focus of the power laser radiation of a distance p inside the tissue to be perforated, the absence of any impingement on the local configuration surrounding that tissue being maintained. As a matter of fact, as it will be disclosed in more details in the following description, the preceding operative steps are performed by means of the visible radiation of low energy only. The ultimate operative step appears to be then generating at least one power laser radiation pulse, directed and focussed on the tissue to be treated.

Figure 1B:
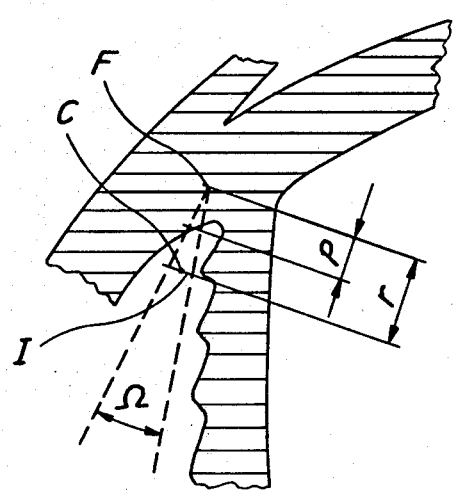
FIG. 1b represents an enlarged view in perspective of the region of the eye submitted to the laser beam treatment according to the invention.
Figure 2A:
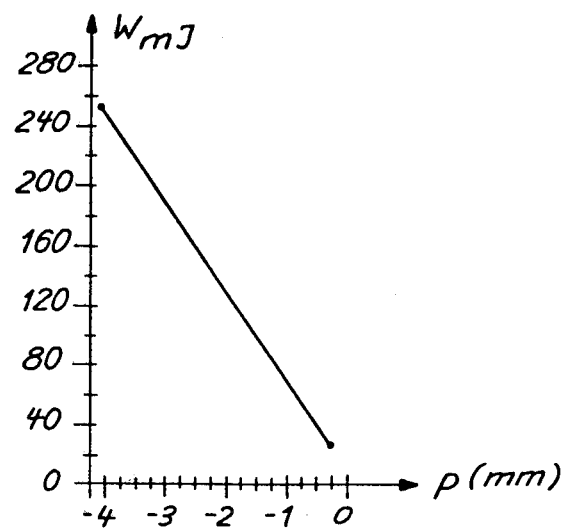
FIG. 2a represents as an example the diagram of the curve of the distance of the focussing point of the power laser radiation with respect to the wall to be perforated, as a function of the radiated energy of each laser impulse.
Figure 2B:
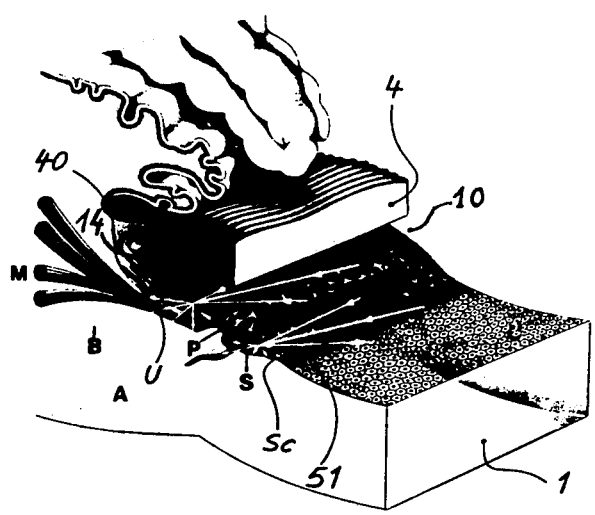
FIG. 2b represents, according to a section of FIG. 1a, the preferential regions of focussing of the laser beam.

In accordance with the method of the invention as shown in FIG. 1b, the laser radiation is focussed at its maximal value in relation with local configuration according to a solid angle $\Omega$ determining a radiated power density above or equal to $2 \times 10^{10}$ Watts/cm$^2$ at a distance r from the determined point of focussing F. This focussing probably favours a stabilisation of the ionisation zone I and of the centre of ionisation C of the propagating medium. As shown in FIG. 1b, after the operative step of shifting, the laser radiation is focussed at F inside the wall to be perforated, the distance p from the focussing point F of the laser radiation at the entry surface of the wall to be perforated being substantially close to the mean distance r separating the ionisation zone from the laser point of focussing F. Thus, taking into account the moderate increase in temperature of the propagation medium as mentioned previously, the wall is perforated very probably by the effect of the shock wave. As an example, according to tests carried out from a Q switched Nd-YAG laser of emmission wavelength of 1.06 $\mu$m, the wavelength of emission, without departing from the scope of the present invention, able to be comprised between 0.4 and 2 $\mu$m, the laser radiation is focussed at a distance p from the entry surface inside the wall to be perforated, varying, as a proportion of the radiated energy of each pulse i.e. according to a law that is substantially linear. By way of non-limitative example, for laser pulses of radiated energy comprised between 300 millijoules and 30 millijoules, the distance of focussing p counted negatively with respect to the face of the wall to be perforated as shown in FIG. 2a, is inferior to 4 mm. Such a focussing, as a function of the energy of emission, probably allows there to be obtained perforations of the same optimum configuration for a same treated tissue. The treated tissue can, according to the final diagnosis of the doctor, be situated for example in the case of chronic glaucoma simplex, in the irido-corneal angle 14 on the level which the canal of Schlemm S as shown in FIG. 2b. The power laser radiation 51 is directed and focussed on the trabecular meshwork T inside the region of the Schwalb's ring Sc. In this case, the treatment by laser beam allows the opening of a communication between the canal of Schlemm S and the anterior chamber of the eye 10.

Figure 3A:
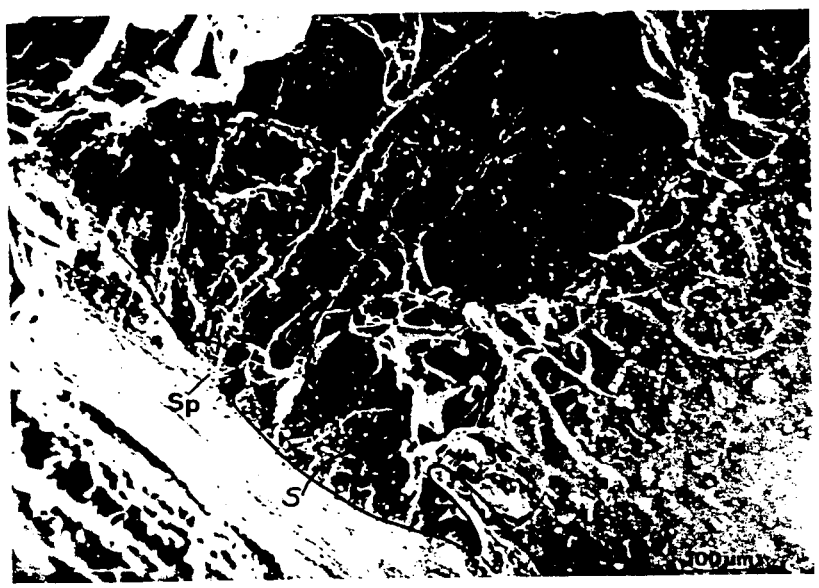
FIGS. 3a and 3b represent an example of the perforation obtained by irradiation, according to the method of the invention, of the irido-corneal angle of the eyeball of a Macaca Speciosa monkey.

As shown in FIG. 3a, after irradiation of the anterior chamber of the eye of a Macaca Speciosa monkey, preparation of the tissues fixed by a solution at 1% of osmium tetroxide, then drying and deposit by vaporisation of a layer of gold of 300 Å thickness and observation by electronic microscope, the trabecular meshwork T, having been cut by the shock wave, has shrunk, leaving a largely open communication, the cells of the external wall of the canal of Schlemm S being destroyed whereas the collagen fibres of the sclerotic have practically not suffered.

Figure 3B:
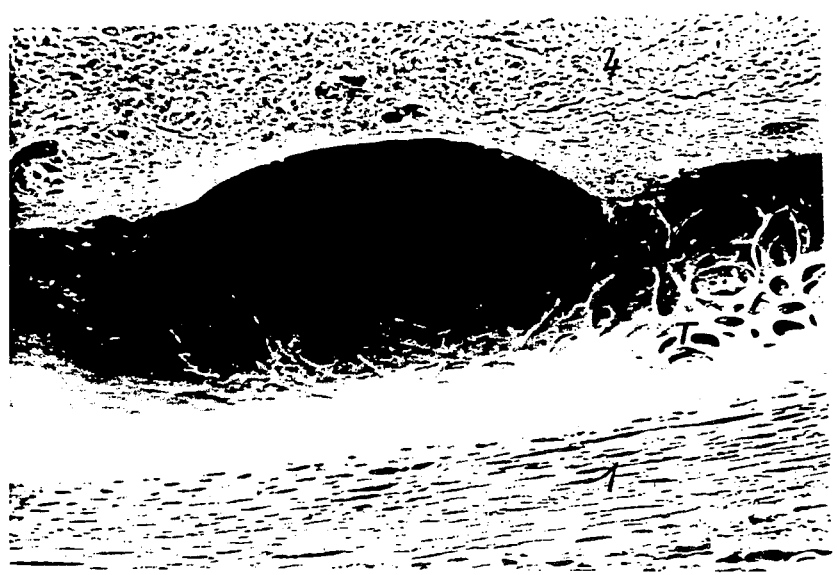

In the case of glaucoma simplex, the treated zone can also be situated in the centre of the "uveal trabeculae" extending close to the root of the iris 4 as shown at U in FIG. 2b. In this case the treatment by laser allows, as shown in FIG. 3b, a cyclodialysis or opening of the supra-ciliary space. FIG. 3b shows a cyclodialysis 16 months after irradiation in the region U (FIG. 2b) of the irido-corneal angle of the anterior chamber of the eye of a Macaca Speciosa monkey after enlargement. As in FIG. 1a, 4 represents the iris, 1 the cornea and T the trabecular meshwork.

A series of laser pulse impacts leaving the end of the cornea 1 and being directed towards the root of the iris simultaneously allows the opening of the canal of Schlemm S together with the opening of the supra-ciliary canal Sc and cyclodialyses, without departing from the scope of the method of the invention.

The method for the surgical treatment of the anterior chamber of the eye in case of glaucoma is not limited ot the perforation of the zone of the irido corneal-angle, the method also being able to be carried out in the case of glaucoma with closed angle by perforating the iris. In such a case, the distance p for the shifting of the focussing point of the power laser radiation is substantially inferior to 2 mm, thereby allowing an iridotomy or iridectomy. These can also be performed in the case of intermittent glaucoma.

The mixed form of glaucoma can also be treated according to a particular embodiment of the method of the invention. In such a case, the method for surgical treatment substantially comprises as example the two following steps.

The angle of the anterior chamber of the eye is chosen as first tissue to be perforated and then the corresponding operative steps are carried out on that first tissue. The iris is then chosen as second tissue to be perforated and the corresponding operative steps are again carried out on that second tissue. As a matter of fact the choice of the tissues can be reversed without prejudice so that the first tissue and second tissue become the iris and the angle of the anterior chamber. The choice may be influenced by the final diagnosis itself.

One of the most important case of glaucoma is to be seen with infantile glaucoma in which classical surgical treatment is to be delayed for months after birth. In such a case the tissue to be treated appears to be the embryonary substance deposited on the walls of the angle of the anterior chamber of the eyeball. The method of the invention allows thus such a deposit to be eliminated and the free circulation of the aqueous humor to be reset immediately after diagnosis.

Another important case of glaucoma to be treated of a certainty appears to be glaucoma related to an inflammation of the supraciliary space and of the iris, such an inflammation leading to the sticking of the iris-root on the walls of the angle of the anterior chamber of the eye. In such a particular case, the power laser radiation is preferably focussed on the vicinity of this sticking, thereby allowing this latter to be exploded.

Another glaucoma case of interest for treatment according to our invention appears to be the so-called glaucoma by obstruction of the pupillary block. The power laser radiation is then focussed on the iris in order to perform an iridotomy for the re-establishment of the free circulation of the aqueous humour.

In many other cases of glaucoma such as glaucoma induced through occlusion pupillae by a membrane grown due to inflammation, focussing the power laser radiation in the same way as for glaucoma by obstruction of the pupillary block will lead also to re-establishment of free circulation of the aqueous humour.

As an example all of these operations can be carried out with the aid of a system of laser emission Nd-glass in the Q switched mode of emission wavelength substantially equal to 1.06 μm and of energy of the laser pulses emitted of 110 m J at the exit of the focussing lens, the energy in fact reaching the treated zone after reflections and losses in the different media being estimated at 60 m J and the pulse having a duration measured as half power of 35 ns.

The laser emission beam will have preferably a distribution of light intensity as a function of the distance with respect to the optical axis of the beam, substantially similar to a Gauss curve. The mode of laser emission is the TEMoo mode in this case.

Figure 4A:
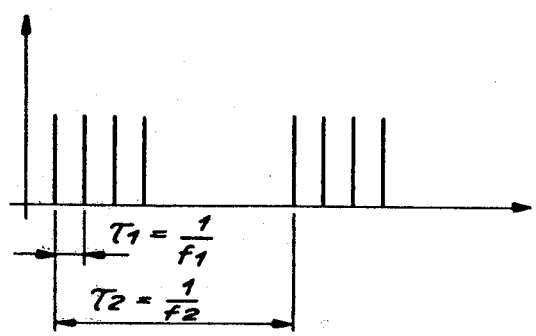
FIGS. 4a and 4b represent a variant of emission of laser radiation by modulation of the emission beam and an apparatus allowing the method of our invention to be performend.

According to FIG. 4a the laser pulses are generated by pulse trains or bursts. The repetition frequency $f_1$ of the pulses is comprised between 50 kHz and 10 MHz. The trains of pulses themselves are generated at a repetition frequency $f_2$ less than 200 Hz.

Figure 4B:
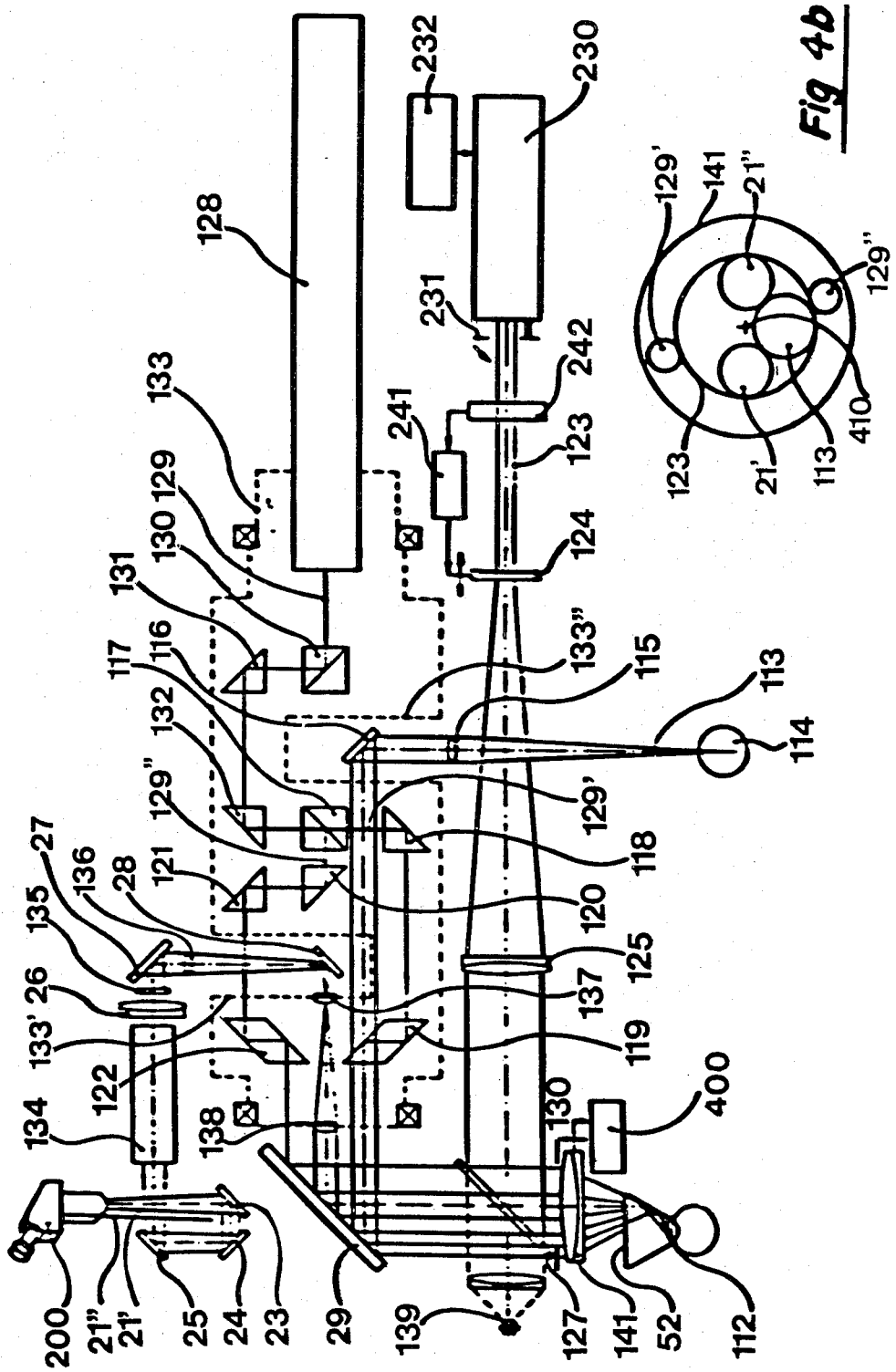

Such pulses can, for example, be emitted in accordance with the device for the treatment of glaucoma described and shown FIG. 4b.

According to FIG. 4b, the optical observation beams are shown by zone 21', 21". On issuing from the binocular 200, the beams are consecutively reflected by mirrors 23, 24, 25 until they reach the converging lens 26 whose focus is the focus of the binocular 200. On issuing from lens 26 the optical observation beams are now parallel beams and are reflected by the mirrors 27, 28, 29 in order to be brought coaxially upon the focussing lens or objective 141. The optical observing beams are focussed by that last focussing lens 141 across the contact glass 51 see FIG. 1a upon the zone or point of observation 112 of the patient's eye. In the present case, the observation point 112 is the irido-corneal angle. An optical illuminating beam 113 issues from block 114 consisting of a light source (incandescent lamp, arc light or discharge light). The illuminating beam 113 is forced to be parallel by a converging lens 115 whose focus is disposed in the plane of a diaphragm of block 114. The illuminating beam 113 is then reflected by the mirror 116 and 29, then arrives at the focusing lens 141 where it is focussed on to the observation point 112. The device according to FIG. 4b includes also a laser beam generator 230 for the surgical treatment of the eye. The laser treatment-beam actuating the surgical operation is shown at 123. It may issue for instance from a solid state laser at Q switched mode. The wave length will be typically close to 1 μm. A Nd-YAG laser for example emits mainly at 1.06 μm. The laser treatment beam is enlarged by lens 124, rendered parallel by lens 125 and focussed by converging lens 141. The laser treatment beam is superimposed upon the optical observation beams 21', 21" by means of a reflecting surface 127. This surface may consist of a mirror or an interference lamella which only reflects a very faible band with around laser treatment beam wave length. A controlled device 400 allows the displacement of lens 141. An ancillary device aids in the exact determination of the focal plane of lens 141. It is a continual laser source 128 of low energy, for example a He-Ne Laser. The emitted visible laser beam 129 is directed across the reflecting surfaces 130, 131, 132 (prisms or mirrors) towards a beam splitter 117 where it is divided into beams 129', 129" which after reflection on mirrors 118, 119, 120, 121 and 29 will reach both lens 141 through mirror 127. After leaving lens 141, visible beams 129' and 129" will substantially follow the same optical path as that one of laser treatment beam 123. The divided laser beams 129' and 129" are focussed by lens 141 into its focus. Each of the incident beams 129', 129" causes upon the tissue of the eye a bright spot. The focal plane of lens 141 is then located perfectly on the surface of the tissue in the eye while spots of beam 129' and 129" coincide and superimpose on the surface of the tissue. The system 400 constituted of a manual displacement system driver by a micrometric screw allows the precise setting of focal plane of lens 141 on the surface of the tissue. The device according to FIG. 4b is further provided with a command system 241 for the displacement along its optical axis of the divergent lens 124. This lens is coupled to an attenuator 242 acting on the intensity of the laser treatment beam 123. A control system 232 together with a shutter 231 allow the number of pulses received by the patient to be selected. Shutter 231 may be embodied through any opto-electronic device since control system may be one of the kind described in the U.S. Pat. No. 4,039,823 granted to the applicant. Visible laser beams 129' and 129" are adapted to rotate around optical axis 410 of lens 141, thereby generating an envelope of laser treatment beam 123 down stream toward lens 141.

In FIG. 4b 133 designates a tube in which the optical components embodying the device are placed, 133' and 133" designates splits into this tube allowing observating beams 21', 21" and illuminating beam 113 to enter this tube respectively. Reference 134 denotes an image inverter which produces a real image, and reference 135 designates a filter absorbing all parasitic radiation that may arise from laser treatment beam reflection. The references 136, 137, 138 designates lenses or objectives which form together an optical relay allowing the substantial conservation of light on a long parallel path.

References 139 and 139' designate a detector and an associated converging lens allowing measurement and direct control of the temporal and energetic transmission characteristics of the laser treatment beam through mirror 127. An adjustable diaphragm 140 is associated with converging lens 141 for the adjustment of the focussing solid angle of laser treatment beam 123. Accordingly mirrors 118, 132 are adapted to be moved towards each other to keep visible laser beams 129' and 129" adjacent with laser treatment beam 123 according to its diameter. This diameter is thus given by that of adjustable diaphragm 140. Tube 133 is rotatable around its longitudinal axis given by optical axis of lens 138 or visible laser beam 129.

The preceding operative steps for carrying out the method of our invention can be performed with a very high accuracy by using the above mentioned device.

For such a purpose, the doctor will have to select and fix the focussing solid angle of the laser treatment beam 123 at its maximal value according to his final diagnosis after the careful examination of the angle of the anterior chamber of the eye together with its surroundings by means of the binocular 200. This operative step can be done by selecting the corresponding diameter of the diaphragm 140. The following operative step consisting in adjusting the focus of the power laser radiation on the tissue to be treated can in turn easily be done by the doctor by using the ancillary visible radiation 129', 129" of low energy that substantially propagates along the same optical path as that of laser treatment beam after lens 141. During the whole duration of the operative steps, except fixing the focussing solid angle of laser treatment beam, the doctor will have to maintain the contact-glass 52 on the eye ball of the patient while carefully examining the focussing point 112 of the laser treatment beam through the binocular 200. Checking the absence of any impingement of the laser treatment beam will be done by making the same operation on the visible radiation through binocular 200 since these have substantially the same optical path. Shifting the focus can then be done by the doctor, while examining through the binocular 200 by shifting divergent lens 124 through command system 241. The laser operative step, i.e. the generation of at least one power laser radiation pulse can be done by firing the control unit system 232. It is worthy of note that examining the angle of the anterior chamber of the eye can be performed at the doctor's will before firing, during firing or after firing to check the power laser radiation impact on the tissue to be treated since the laser treatment beam wavelength, particularly in case of Nd-YAG laser, will not be seen by the doctor or will be cut off by filter element 135.

What is claimed is:

1. For a method of non-invasive surgical treatment of the eye which comprises the steps of
   forming a convergent treatment laser beam,
   directing the focus of the convergent treatment laser beam onto the structure to be treated,
   shifting the focus with respect to the structure to be a certain distance in front of or behind the structure,
   delivering the treatment laser beam into said focus where the radiation intensity performs the surgery,
   an improvement to prevent damage to the structure of the eye not being treated, the improvement comprising the steps of:
   generating visible ancillary lower power laser observation beams to sense the outside envelope of the treatment laser beam,
   rotating said laser observation beams around the optical axis of said laser treatment beam, said laser observation beams intersecting in the focus position of the laser treatment beam,
   shifting the focus position of the treatment bean along the optical axis with respect to the intersection point of said laser observation beams,
   directing the laser observation beams onto treatment point of the structure to be irradiated so that they intersect said structure and provide dots of light thereon for observation purposes,
   inspecting the path of the observation laser beams to determine if the treatment beam on its pass into the focus will touch eye structure not being treated,
   adjusting the treatment laser beam in accordance with the results of the inspection step to ensure that the treatment beam does not touch structures not to be treated, and
   delivering the treatment laser beam into the focus to cause the surgery.

2. A method for surgical treatment of the eye as claimed in claim 1, wherein the treatment laser beam has a power of between 30 mJ and 300 mJ and a duration of between 10 and 60 ns thereby allowing through ionization in the vicinity of the focus sufficient power to be generated for the perforation of said tissue.

3. A method for surgical treatment of the eye as claimed in claim 2, wherein the treatment laser beam wavelength is between 0.5 $\mu$m and 1.1 $\mu$m.

4. A method for surgical treatment of the eye as claimed in claim 1, wherein said distance is proportional to the energy of said treatment laser beam.

5. A method for surgical treatment of the eye as claimed in claim 4, wherein the distance is less than 4 mm.

6. A method for surgical treatment of the eye as claimed in claim 4, wherein for the treatment of glaucoma with closed angle, the tissue to be perforated is the iris and said distance is less than 2 mm.

7. A method for surgical treatment of the eye as claimed in claim 1, wherein said treatment laser beam comprises a burst of elementary pulses, each burst repeated at a frequency of less than 100 Hz.

8. A method for surgical treatment of the eye as claimed in claim 1, wherein for the treatment of chronic glaucoma simplex, the tissue to be perforated is the irido-corneal angle of the anterior chamber of the eye, the treatment laser beam being focussed inside said tissue.

9. A method for surgical treatment of the eye as claimed in claim 1, wherein for the treatment of mixed glaucoma the steps are:
   perforating first the iridio-corneal angle of the anterior chamber of the eyeball,
   performing the corresponding operative steps on said iridio-corneal angle,
   perforating the iris, and performing the corresponding operative steps on said iris.

10. A method for surgical treatment of the eye as claimed in claim 1, wherein for the treatment of mixed glaucoma in the steps are:
    perforating the iris,
    performing the corresponding operative steps on said iris tissue,
    perforating the iridio-corneal angle of the anterior chamber of the eyeball, and
    performing the corresponding operative steps on said iridio-corneal angle.

11. A method for surgical treatment of the eye as claimed in claim 1, wherein for the treatment of the infantile glaucoma the tissue to be treated is the embryonary substance deposited on the iridio-corneal angle of the anterior chamber of the eyeball.

12. A method for surgical treatment of the eye as claimed in claim 1, wherein for the treatment of secondary forms of glaucoma related to an inflammation of the supraciliary space and of the iris leading to the sticking of the iris root with the walls of the angle of the anterior chamber of the eye, said treatment laser beam is focussed on the vicinity of said sticking.

13. A method for surgical treatment of the eye as claimed in claim 1, wherein for the treatment of glaucoma by obstruction of the pupillary block, the tissue to be perforated is the iris.

* * * * *